(12) United States Patent
Habets (10) Patent No.: US 10,379,447 B2
(45) Date of Patent: Aug. 13, 2019

(54) METHOD AND APPARATUS FOR SIMULATION OF LITHOGRAPHY OVERLAY

(71) Applicant: Boris Habets, Dresden (DE)

(72) Inventor: Boris Habets, Dresden (DE)

(73) Assignee: Qoniac GmbH, Dresden (DE)

( * ) Notice: Subject to any disclaimer, the term of this patent is extended or adjusted under 35 U.S.C. 154(b) by 601 days.

(21) Appl. No.: 13/938,720

(22) Filed: Jul. 10, 2013

(65) Prior Publication Data

US 2015/0019192 A1    Jan. 15, 2015

(51) Int. Cl.
  *G03F 9/00* (2006.01)
  *G01N 21/95* (2006.01)
  *G03F 7/20* (2006.01)

(52) U.S. Cl.
  CPC ..... *G03F 7/70633* (2013.01); *G01N 21/9501* (2013.01); *G03F 7/705* (2013.01); *G03F 9/7003* (2013.01); *G03F 9/7046* (2013.01); *G03F 9/7088* (2013.01)

(58) Field of Classification Search
  None
  See application file for complete search history.

(56) References Cited

U.S. PATENT DOCUMENTS

| | | | | |
|---|---|---|---|---|
| 6,686,107 B2 * | 2/2004 | Matsumoto | ........... | G03F 9/7011 430/22 |
| 7,009,704 B1 * | 3/2006 | Nikoonahad | ....... | G03F 7/70633 356/399 |
| 7,556,899 B2 * | 7/2009 | Ikeda | ................... | G03F 7/70633 382/151 |
| 7,571,420 B2 * | 8/2009 | Wong | .................. | G06F 17/5009 716/54 |
| 7,783,444 B2 * | 8/2010 | Habets | .................... | H01L 21/68 702/81 |
| 7,804,580 B2 * | 9/2010 | Kono | .................... | G03F 9/7096 355/30 |
| 7,804,596 B2 * | 9/2010 | Yoo | ..................... | G03F 7/70633 356/401 |
| 8,143,731 B2 * | 3/2012 | Chiu | .................. | G03F 7/70633 257/797 |
| 8,440,475 B2 * | 5/2013 | Habets | .................... | G03F 7/705 324/500 |

(Continued)

FOREIGN PATENT DOCUMENTS

WO    2010020331    2/2010

OTHER PUBLICATIONS

Chen "Overlay modelling for proximity x-ray lithography", Journal of Vacuum Science and Technology B 1998, pp. 3485-3490.

*Primary Examiner* — Kibrom K Gebresilassie
(74) *Attorney, Agent, or Firm* — 24IP Law Group USA, PLLC; Timothy R DeWitt (57) ABSTRACT

A method for simulation of lithography overlay is disclosed which comprises storing alignment parameters used to align a semiconductor wafer prior to a lithography step; storing process control parameters used during the lithography step on the semiconductor wafer; storing overlay parameters measured after the lithography step; calculating alternative alignment parameters and alternative process control parameters. The alternative alignment parameters and the alternative process control parameters are added to cleansed overlay parameters to obtain simulated lithography overlay data.

9 Claims, 5 Drawing Sheets

(56) References Cited

U.S. PATENT DOCUMENTS

| | | | |
|---|---|---|---|
| 8,874,249 B2* | 10/2014 | Ausschnitt | G03F 7/705 428/14 |
| 8,982,320 B2* | 3/2015 | Okita | G03F 7/70633 355/53 |
| 9,087,176 B1* | 7/2015 | Chang | G06F 17/5081 |
| 2002/0183989 A1 | 12/2002 | Chien | |
| 2003/0002043 A1* | 1/2003 | Abdulhalim | G03F 7/70633 356/400 |
| 2005/0154484 A1* | 7/2005 | Lee | G03F 7/705 700/121 |
| 2005/0157297 A1* | 7/2005 | Abdulhalim | G03F 7/70633 356/401 |
| 2005/0209818 A1* | 9/2005 | Chao | G03F 7/70483 702/182 |
| 2007/0021860 A1* | 1/2007 | Gertrudus Simons | G03F 7/70516 700/121 |
| 2008/0057418 A1* | 3/2008 | Seltmann | G03F 7/70633 430/30 |
| 2008/0228435 A1 | 9/2008 | Lee | |
| 2009/0248337 A1* | 10/2009 | Habets | H01L 21/68 702/81 |
| 2009/0303482 A1* | 12/2009 | Levinski | H01L 21/68 356/400 |
| 2010/0030360 A1* | 2/2010 | Habets | G03F 7/705 700/110 |
| 2010/0185311 A1 | 7/2010 | Hsieh | |
| 2011/0053060 A1* | 3/2011 | Tsubata | G03B 27/42 430/30 |
| 2011/0196646 A1* | 8/2011 | Mos | G03F 7/705 702/150 |
| 2012/0191236 A1* | 7/2012 | Ausschnitt | G03F 7/705 700/105 |
| 2013/0258308 A1* | 10/2013 | Sakamoto | G03F 7/70775 355/72 |
| 2014/0065528 A1* | 3/2014 | Kasa | G03F 9/70 430/30 |
| 2016/0018741 A1* | 1/2016 | Liou | G03F 7/70633 355/52 |
| 2017/0277044 A1* | 9/2017 | Lee | G03F 9/7034 |

* cited by examiner

METHOD AND APPARATUS FOR SIMULATION OF LITHOGRAPHY OVERLAY

CROSS-REFERENCE TO RELATED APPLICATIONS

The present application claims the benefit of the filing date of U.S. Provisional Patent Application Ser. No. 61/669,372 filed by the present inventor on Jul. 9, 2012.

The aforementioned provisional patent application is hereby incorporated by reference in its entirety.

This patent application additionally is related to U.S. Non-Provisional application Ser. No. 13/749,740 entitled "Method and Apparatus for Fabricating Wafers" and filed on 25 Jan. 2013, Now U.S. Pat. No. 9,543,223, which hereby is incorporated by reference herein.

FIELD OF THE INVENTION

This field of the present application relates in general to a method for the simulation of a lithography overlay and an apparatus for the simulation of a lithography overlay on the surface of a semiconductor wafer.

BACKGROUND OF THE INVENTION

It will be appreciated that the term "semiconductor wafer" as used in this disclosure is intended to imply wafers used in the manufacture of all types of semiconductor devices, including, but not limited to, memory devices, ASICS, liquid crystal panels, and photovoltaic devices.

Current trends in the processing of the semiconductor wafers means that overlay budgets shrink with shrinking ground rules, and manufacturing processes are becoming more aggressive. Non-limiting examples of such aggressive manufacturing processes include high aspect ratio etching or deposition of exotic materials on a surface of the semiconductor wafer. The non-uniformity of some manufacturing processes over the semiconductor wafer surface and a plurality of manufacturing process steps may result in non-uniform stress being applied to the semiconductor wafer. When the semiconductor wafer deforms from one manufacturing process step to a subsequent manufacturing process step, e.g. from one lower layer to a subsequent layer on top of the lower layer, patterns in the upper layer may become misaligned to patterns in the lower layer. For the error free functioning of a semiconductor the relative position of patterns on the different layers to each is relevant. These relative positional errors are termed "overlay errors". The need for smaller and denser structures on the semiconductor wafer means that an allowable tolerance for the overlay errors decreases.

The overlay error is determined by means of so-called "overlay marks". In a lower layer together with the pattern for the semiconductor structure of the process step a first overlay mark is exposed in a photoresist film. After developing and processing this lower layer, the first overlay mark becomes part of the structure of this lower layer. On a higher layer in a subsequent process step together with the pattern for the semiconductor structure of the higher layer, a second overlay mark is exposed in a photoresist film. After development of the photoresist film the relative position error between the first overlay mark on the lower layer and the second overlay mark on the top layer can be measured in an overlay measurement tool. If the tolerance of the overlay error is too large the semiconductor wafer may be reworked with applied corrections. The goal is to use the measured overlay errors to compensate for the overlay errors in a next lot of semiconductor wafers, so as to minimize the overlay errors in the next lot and thus avoid costly rework.

From U.S. Patent Application Publication No. 2010/0030360 a method of calculating "alignment" residuals in a fabrication unit is known that comprises providing an alignment model including alignment model parameters; providing an exposure tool suitable for exposing a lot of semiconductor wafers in a plurality of exposure fields; retrieving alignment data comprising alignment values, measured by the exposure tool on the semiconductor wafers of the lot at a plurality of positions of the exposure fields that are used to calculate values for the alignment model parameters of the alignment model; calculating a set of alignment residuals from the alignment data by subtracting effects of the alignment model parameters for each of the plurality of measured positions and for each of the semiconductor wafer in the lot; and issuing a warning signal based upon a comparison between the set of alignment residuals and a set of reference values. The U.S. '360 document further comprises a system for calculating alignment residuals and a computer readable medium including instructions capable of performing the steps of calculating alignment residuals on a computer.

Ideally overlay measurements should be taken for each one of the semiconductor wafers at multiple positions on each exposure field on each of the semiconductor wafers to achieve a degree of precision and thus to achieve high yield rates for the fabrication of the semiconductor wafers. However, complete overlay measurements are very slow to perform, so they may cause a tool capacity problem. In other words, the time taken to perform a complete overlay measurement is a multiple of the time taken to process the semiconductor wafer. Thus, in order to provide the overlay measurements of each of the semiconductor wafers, a number of overlay measurement units has to be provided to distribute the overlay measurements on several parallel organised overlay measurement units.

The overlay measurement units are a significant cost factor in a semiconductor manufacturing process and for cost reasons the deployment of the parallel arranged overlay measurements units is avoided. Another solution for reducing limitations in the semiconductor manufacturing process whilst not extending the number of the overlay measurement units is to measure the overlay measurements in only a subset of the semiconductor wafers.

A reduction in the number of overlay measurements will increase the throughput of the semiconductor process. However, there will be a resultant reduction in the accuracy of the measurements and thus a reduction in the reliability of any values calculated from an interpolation of the measurements. This will not be serious if the absolute value of the overlay measurements only varies a little across the surface of the wafer. This assumption is not always valid.

Currently the only way of verifying the assumption is to carry out experiments which involve time and reduce the throughput of the semiconductor process.

SUMMARY OF THE INVENTION

The teachings of the disclosure provide a method for simulation of lithography overlay that enables simulations of alternative overlay measurements to be carried out. This in turn allows the testing of assumptions regarding the number of measurement that need to be carried out as well as potentially providing a control method for optimising the throughput of the lithography process.

The method comprises storing alignment parameters used to align a semiconductor wafer in an exposure device prior to a lithography step, storing process control parameters used during the lithography step and storing overlay parameters measured after the lithography step. An alternative alignment model is defined and alternative alignment parameters and alternative process control parameters are calculated. The alignment parameters and the process control parameters are subtracted from the stored overlay parameters to produce cleansed overlay measurement data. The alternative alignment parameters and the alternative process control parameters are added to the cleansed overlay measurement data to obtain simulated lithography overlay data.

The alternative alignment parameters and alternative process control parameters generated from the alternative alignment model can be used to test alternative alignment strategies and alternative measurement strategies and thus allow a semiconductor process engineer to optimise the throughput of the semiconductor production process.

In one aspect of the invention, the alternative process control parameters can be fed to the exposure device. In a further aspect of the invention, the simulated lithography overlay data can be visualized on a visualization device to enable the semiconductor process engineer to understand the process.

The disclosure also teaches an apparatus for simulation of a lithography process on a surface of a semiconductor wafer. The apparatus comprises a non-volatile data store for storing alignment parameters used to align a semiconductor wafer prior to a lithographic step, process control parameters used during the lithography step as well as measured overlay data received from an overlay measurement tool. The apparatus includes a simulation processor for determining an alternative alignment model and calculating, from the alternative alignment model, alternative alignment parameters and alternative process control parameters. The simulation processor is further configured to subtract the stored alignment parameters and the stored process control parameters from the measured overlay data to obtain cleansed overlay data. Subsequently the simulation processor adds the alternative alignment parameters and the alternative process control parameters to the cleansed overlay data to obtain simulated overlay measurement data.

It will be appreciated that the semiconductor wafer can be a wafer for microelectronic circuits, such as memory devices or ASICS, liquid crystal panels as well as photovoltaic devices.

DETAILED DESCRIPTION OF THE INVENTION

The invention will now be described on the basis of the drawings. It will be understood that the embodiments and aspects of the invention described herein are only examples and do not limit the protective scope of the claims in any way. The invention is defined by the claims and their equivalents. It will be understood that features of one aspect or embodiment of the invention can be combined with a feature of a different aspect or aspects and/or embodiments of the invention.

In the following, embodiments and/or implementations of the method and the apparatus are described with respect to simulating overlay measurements during a lithography step whilst manufacturing a semiconductor device on a semiconductor wafer. The embodiments, however, might also be useful in other respects, e.g., improvements in process control, improvements in identifying lot to lot variations of a layout pattern, yield enhancement techniques or the like.

Furthermore, it should be noted that the embodiments and/or implementations are described with respect to semiconductor wafers but might also be useful in other respects including but not limited to thin film elements. Other products, e.g., liquid crystal panels, ASICS, photovoltaic devices, or the like might be produced as well.

Figure 1:
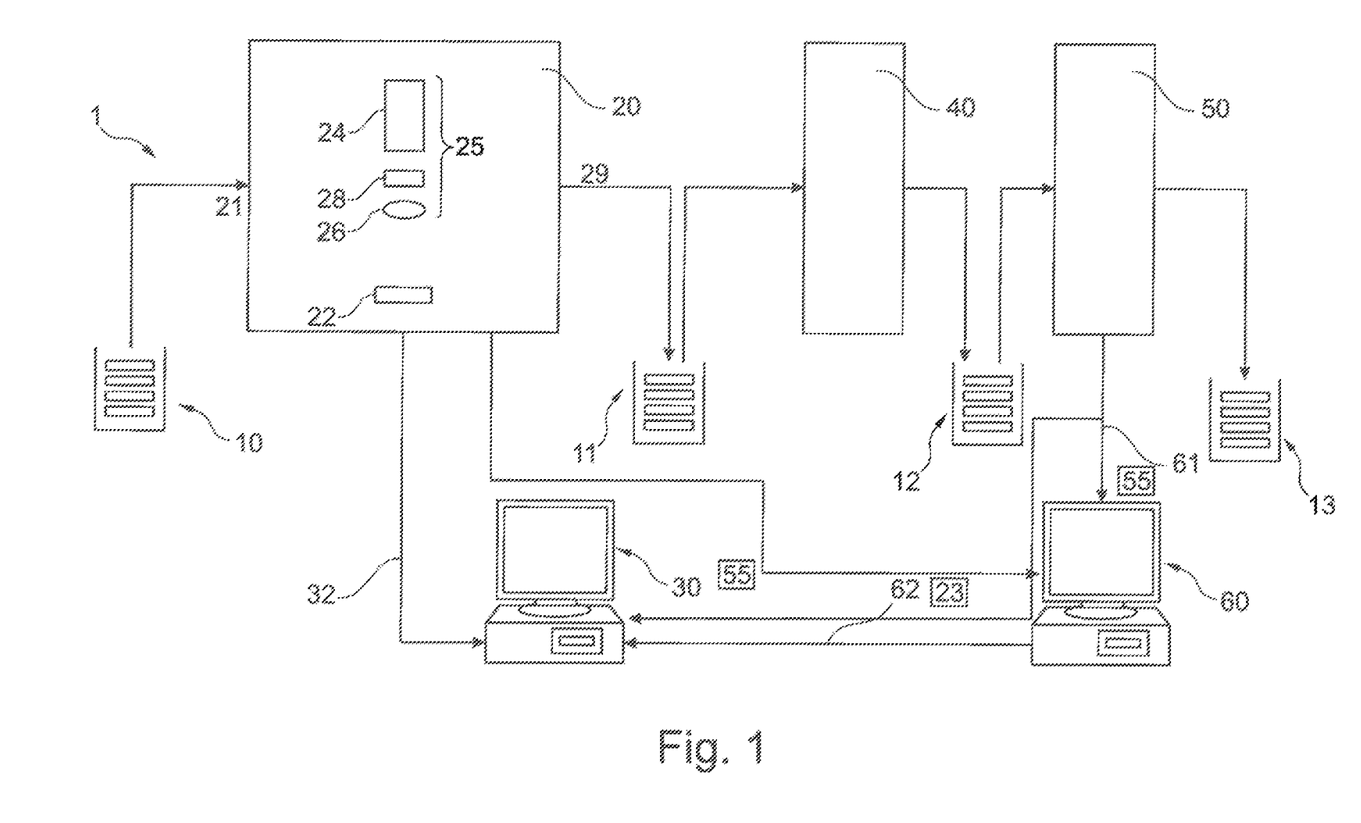
FIG. 1 shows a first aspect of the present disclosure

FIG. 1 shows in a schematic view a fabrication unit 1 for patterning a surface of a semiconductor wafer 10 and performing an overlay calculation and simulation. The fabrication unit 1 forms part of a semiconductor manufacturing system. The fabrication unit 1 comprises an exposure tool 20 for aligning and exposing portions of the surface of the semiconductor wafers 10, an exposure controller 30, a developing unit 40 for developing exposed ones of the semiconductor wafers 11, and an overlay measurement tool 50. The fabrication unit 1 also includes a simulation processor 60 shown here as a stand-alone computer, but which could be running as a software module on a server, in a cloud computer or on a local computer. The simulation processor 60 includes non-volatile memory for storage of data. The exposure controller 30 also includes a unit sometimes termed a R2R or run-to-run controller.

A plurality of semiconductor wafers 10, usually referred to as a lot, is loaded into the exposure tool 20. The semiconductor wafers 10 loaded into the exposure tool 20 have been coated with a photoresist film in a preceding process step. The exposure tool 20 includes a load port 21 for loading the semiconductor wafers 10 and an unload port 29 for unloading exposed ones of the semiconductor wafers 11. Within the exposure tool 20 the semiconductor wafers 10 are placed on a substrate holder 22.

Figure 2A:
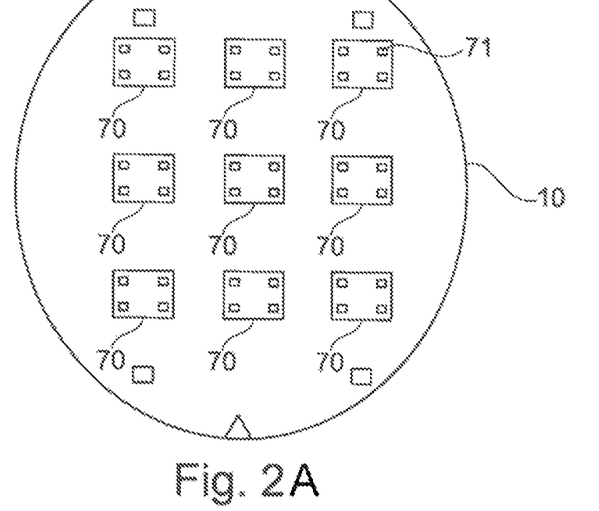
FIG. 2A shows wafer with exposure fields
Figure 2B:
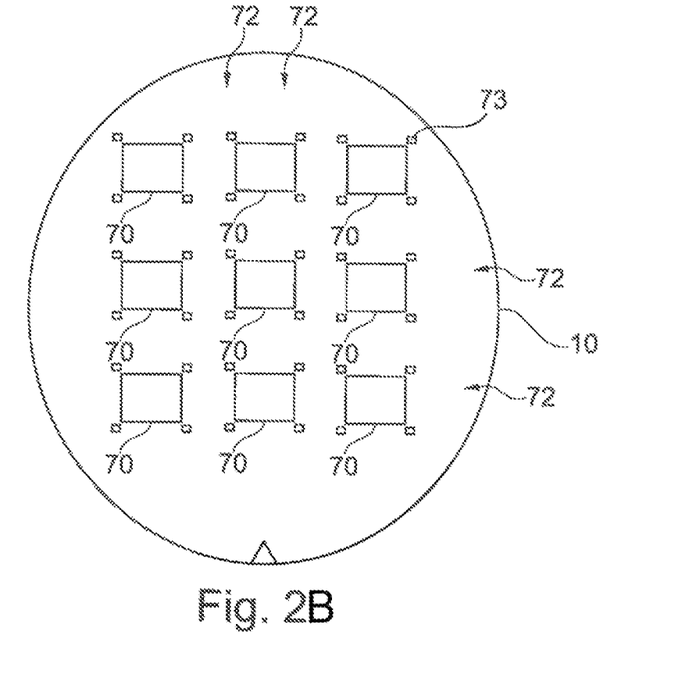
FIG. 2B shows another wafer with exposure fields

A typical one of the semiconductor wafers 10 comprises a plurality of exposure fields 70 arranged on the semiconductor wafer 10 in a grid-like pattern, as schematically shown in FIG. 2. The plurality of exposure fields 70 usually are exposed one exposure field 70 after another exposure field 70. The substrate holder 22 is positioned by actuators (not shown) within the exposure device 20 at least in two dimensions to move the semiconductor wafer 10. Thus each one of the exposure fields 70 on the semiconductor wafer 10 is positioned in turn using a projection system 25 as the semiconductor wafer 10 is stepped back and forth, and up and down within the substrate holder 22. The projection system 25 comprises a light source 24, a projection optic 26, and a photo mask 28. The semiconductor wafer 10 includes alignment marks that are used by the exposure tool 20 to align the surface of the semiconductor wafer 10 with the light source 24 and the projection optic 26 to ensure that the correct exposure field 70 is illuminated. Alignment data 23 from the alignment of the semiconductor wafer is generated by the exposure tool 20 and this alignment data 23 is transferred to the simulation processor 60.

Each time the semiconductor wafer 10 and the projection system 24, 26, 28 have been aligned, the photo mask 28 is illuminated with the light source 24 and the pattern from the photo mask 28 is projected on each individual exposure field 70 one exposure field at a time. The pattern on the photo mask 28 is used to generate a structure of one layer of the semiconductor device as well as overlay marks 71.

The overlay marks 71 are used to determine overlay correction parameters to be used by the exposure tool 20 to project the photo mask 28 onto the correct portion of the surface of the semiconductor wafer 10 for the exposure field 70. Other ones of the overlay marks 71 will have been generated in a lower layer during a previous process step by a different exposure pattern in a previous photoresist layer during the exposure of the structure for this previous semiconductor layer (i.e. for a lower semiconductor layer). These lower overlay marks 71 in the previous photoresist layer are visible through later (upper) photoresist layers, as the photoresist layer is transparent. These lower overlay marks will be termed "reference marks" 74.

The overlay error is the difference between the expected position of the pattern of the individual exposure field 70 and the actual position of the pattern of the individual exposure field 70. The overlay error is measured in the overlay measurement tool 50, as described below. The overlay error can be corrected between specific pairs of the semiconductor layers of the semiconductor wafer 10. Different reference marks 74 are provided on different ones of the semiconductor layers and it is possible to see different ones of the reference marks 74 through multiple layers.

The overlay error is often due to semiconductor wafer deformations, which are introduced to a semiconductor wafer 10 during the various process steps to which the semiconductor wafer 10 is exposed. The overlay measurement tool 50 calculates overlay correction parameters from the overlay error and passes the overlay parameters to the exposure controller 30 and to the simulation processor 60. The exposure controller 30 determines process correction parameters from the overlay correction parameters and passes the process correction parameters to the exposure tool 20.

The exposure tool 20 uses the process correction parameters to calculate the portion of the semiconductor wafer 10 onto which the pattern is to be projected. The process correction parameters provided by the exposure controller 30 are calculated for each one of the semiconductor wafers 10 (termed wafer fine model correction parameters) and each one of the exposure fields 70 (termed field fine correction parameters) on the semiconductor wafer 10. With the calculated process correction parameters, the semiconductor wafer 10 or the photo mask 28 can be shifted in either one or both of the x-direction or the y-direction, can be rotated around a vertical z-axis, or the projection system may be adjusted to a different magnification by disposing the projection system along the z-axis.

After the mask projection step, e.g. after all of the exposure fields 70 have been exposed with the pattern of the photo mask 28, each fully exposed semiconductor wafer 11 is unloaded via unload port 29 and the next semiconductor wafer 10 of the lot is loaded into the exposure tool 20 via the load port 21. After all of the exposed semiconductor wafers 11 of a lot have been exposed in the exposure tool 20, the entire lot of the exposed semiconductor wafers 11 is subsequently forwarded to a developing unit 40. In the developing unit 40, the exposed photoresist film on the top surface of the exposed semiconductor wafers 11 is developed by developing chemicals that wash away those unexposed areas of the photoresist film. In other words, a pattern of photoresist film is formed on the surface of the semiconductor wafer 10 that is based on whether or not the portions of the surface were exposed to light of the light source 24 passing through the photo mask 28. It will be noted that, for the sake of brevity, intermediate process steps that might be required, such as post-exposure bake and the like, are not discussed.

The lot of the exposed and developed semiconductor wafers 12 is then passed to the overlay measurement tool 50. The overlay measurement tool 0 can be an integral part of fabrication unit 1, although other configurations are conceivable as well. In the actual exposure step the overlay marks 71 that correspond to the reference marks 74 of a specific layer have been exposed to the photoresist layer. After the development step these overlay marks 71 are visible in the developed photoresist layer and are termed photoresist marks 75.

Figure 3A:
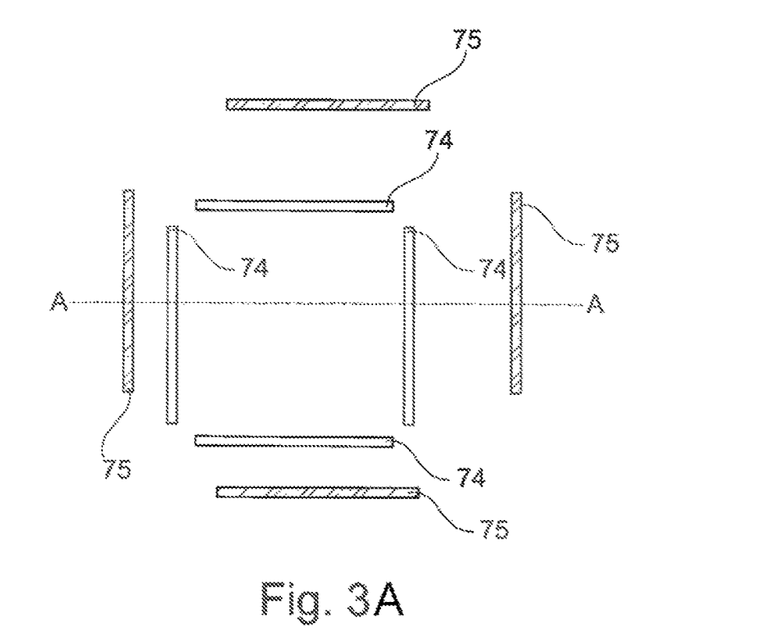
FIG. 3A shows first overlay marks and second overlay marks from a top view
Figure 3B:
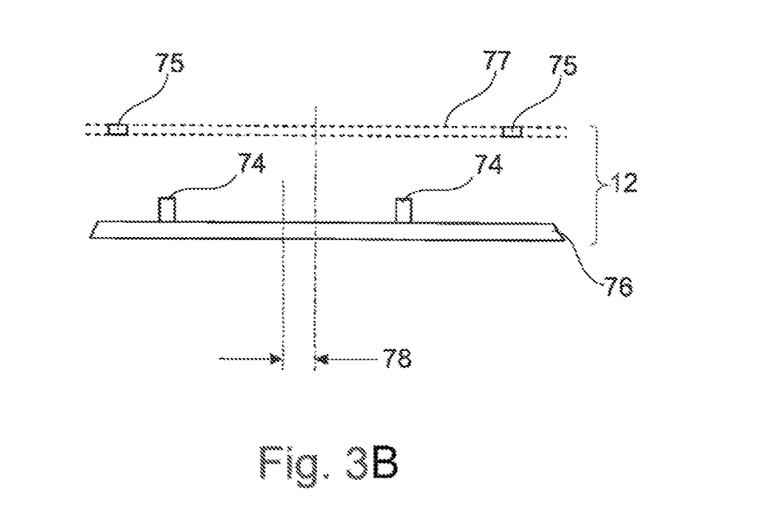
FIG. 3B shows first overlay marks and second overlay marks from a cross-section view

FIG. 3 shows a typical pattern used for the reference marks 74 and the photoresist marks 75. FIG. 3A shows the reference marks 74 and the photoresist marks 75 from a top view and FIG. 3B shows the same reference marks 74 and the photoresist marks 75 as a cross sectional view along the line A-A of FIG. 3A. Some of the reference marks 74 may have been placed initially on the semiconductor wafer 10 at the beginning of the process during a first level lithography or in a special zero level lithography. Other ones of the reference marks 74 (for reasons of clarity not shown in FIG. 3) may have been placed in a later process step on a now intermediate layer.

The reference marks 74 can also be created on the unprocessed semiconductor substrate 76 that will later be part of the semiconductor wafer 10. The semiconductor wafers 10 then undergo many processing steps such as wet etching, dry etching, chemical mechanical planarization (CMP), oxide growth, metal deposition, to name a few. These processing steps change the appearance of the reference marks 74. As the later added layers are substantially transparent the reference marks 74 of different ones of the layers may be simultaneously visible.

The overlay measurement tool 50 measures the relative deviation 78 between corresponding reference marks 74 and photoresist marks 75. The deviations 78 may be measured as deviations in x-direction and y-direction. However, other measurement parameters, such as polar coordinates are conceivable as well.

FIGS. 2A and 2B shows as one aspect of the present disclosure overlay marks 71 that are used on the exposed and developed semiconductor wafer 12. FIG. 2A shows a surface view of four individual overlay marks 71 in each one of the exposure fields 70. FIG. 2B shows a similar figure to FIG. 2A but it is clear from FIG. 2B that there are scribe lines 72 between the various chips, e.g. the various exposure fields 70. The overlay marks 71 are placed within scribe lines 72 in this FIG. 2B.

The overlay measurements on the exposure fields 70 of the semiconductor wafers 10 are done for two reasons. The first reason is to determine the disposition of the photoresist pattern with respect to the lower layers, e.g. determine whether there is a good value of the overlay or whether the overlay error is large. In case the disposition of the photoresist patter is so large that a deposition layer created in the next process step would not match with the layers underneath and would cause a failure of the manufacture semiconductor chip, the photoresist film 77 with the photoresist pattern can be removed from the upper surface of the exposed and developed semiconductor wafer 12. In this case, after removal of the photoresist film 77, the semiconductor wafer 12 can be coated with a new photoresist film 77 and finally can be exposed again in the exposure tool 20 to create a new photoresist pattern.

The second reason for the overlay measurements is to use the overlay measurements to calculate individual process correction parameters for each exposure field 70, which are then used to compensate for process errors (as noted briefly above). The overlay measurement can also be used to simulate overlay corrections.

It is shown in FIGS. 2A and 2B that several overlay marks 71 are created which form a test structure for each exposure field 70 for each single overlay measurement. A common approach is to arrange an overlay mark 71 at each corner of the exposure field 70 and one overlay mark 71 in the middle of each exposure field 70. Other patterns of the test structure are conceivable. The measured deviations between the several overlay marks 71 of a test structure for each exposure field 70 with respect to the reference marks 74 are used to determine a plurality of overlay correction parameters for each individual exposure field 70 as well as overlay correction parameters for the wafer 10. There are at least ten overlay correction parameters which usually are applied:

Wafer translation in x-direction and y-direction ($T_x$, $T_y$)

Wafer magnification in x-direction and y-direction ($M_x$, $M_y$)

Wafer rotation in x-direction and y-direction ($R_x$, $R_y$)

Field magnification in x-direction and y-directions ($FM_x$, $FM_y$)

Field rotation in x-direction and y-direction ($FR_x$, $FR_y$)

The overlay correction parameters $T_x$, $T_y$, $M_x$, $M_y$, $R_x$ and $R_y$ are the wafer fine correction parameters, i.e. they operate at the wafer level. The overlay correction parameters $T_x$, $T_y$, $FM_x$, $FM_y$, $FR_x$ and $FR_y$ are the overlay correction parameters for each of the exposure fields. The overlay correction parameters $T_x$, $T_y$, $FM_x$, $FM_y$, $FR_x$ and $FR_y$ have both a wafer fine component and a field fine component. In other words for each of the exposure fields 70 there is an overlay correction parameter calculated across the whole of the wafer and another overlay correction parameter that is specific to the exposure field 70, as described above.

The overlay measurement toll 50 of the present disclosure measures only a subset of the exposed and developed semiconductor wafers 12 of the whole lot. The measured data of the subset of the exposed and developed semiconductor wafers 12 is used to estimate data for other ones of the exposed and developed semiconductor wafers 12 of the lot that has not been selected for the overlay measurement. A subset for a lot of twenty-five semiconductor wafers for example could comprise three wafers. The number of semiconductor wafers 12 picked for measurement is user configurable as well as the selection strategy. Obviously, the more samples of the semiconductor wafers 12 that are chosen the more accurate the estimated data will be. If the statistical variations of the semiconductor manufacturing process are relatively low, a smaller number of samples of the semiconductor wafers 12 will suffice to obtain sufficiently accurate estimations. If the statistical variations increase the number of selected semiconductor wafers may be increased accordingly. The teachings of this disclosure can be used to simulate the overlay measurements and establish how good the overlay remains with fewer overlay measurements.

The results of the overlay measurement are passed to the simulation processor 60 and to the exposure controller 30. Over time the exposure controller 30 has a history of stored measurements and is able to calculate estimates for the process correction parameters from historical values as well as the new overlay measurement parameters for the semiconductor wafers 10. The calculated process correction parameters are provided to the exposure tool 20 for correcting the exposure alignment for a next lot of the semiconductor wafers 10.

Figure 4:
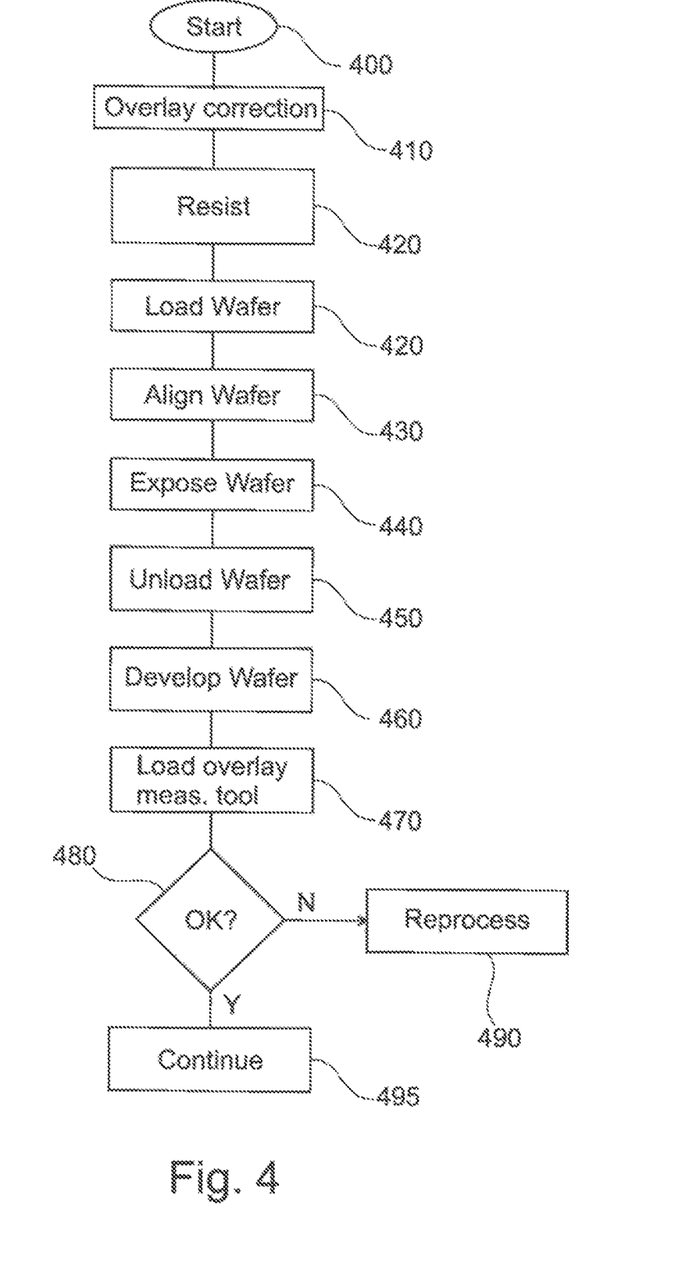
FIG. 4 shows a flow diagram of the method of this disclosure.

The method for simulating the overlay is shown in FIG. 4 and starts at 400. In a first step, 410 an initial set of process corrections is fed into the exposure tool 20 and the semiconductor wafer 10 covered with the photoresist layer in step 420. The initial set of process corrections comprises generally the process correction parameters calculated for the previous lot, but could include newly calculated process correction parameters or simulated process correction parameters that are to be tested in a real environment. In a load step 420, the coated semiconductor wafer 10 is loaded into the exposure tool 20. In an alignment step 430 the semiconductor wafer is aligned in the exposure tool 20 using the alignment marks. The measured alignment data are recorded and passed to the simulation processor 60 for later processing. After alignment, the exposure field 70 of the semiconductor wafer 10 is exposed in exposure step 440 using the set of process corrections with the process correction parameters and the alignment corrections, i.e. the result of the alignment measurement. These process correction parameters and the measured alignment data are stored in the non-volatile memory of the simulation processor 60.

The last two steps are repeated (steps 430 and 440) until all exposure fields 70 of the wafer are exposed in the exposure tool 20. In an unload step 450 the exposed wafer 11 is unloaded and developed in step 460 in the developing unit 30. In this development step 760 the photoresist marks 75 become visible.

The exposed and developed semiconductor wafer 12 is loaded into the overlay measurement device 50 for overlay measurements in step 470. Using the measurement results of overlay measurement step 470 a decision in step 480 is taken whether to discharge the exposed and developed semiconductor wafer 12 for reprocessing in step 490 with wafer with adapted process correction parameters or to pass the exposed and developed semiconductor wafer 12 to the next process step 495. The overlay measurement results are passed to the simulation processor 60 and also to the exposure controller 30. As noted above the exposure controller 30 can use the overlay measurement results to calculate new or amended process correction parameters.

Figure 5:
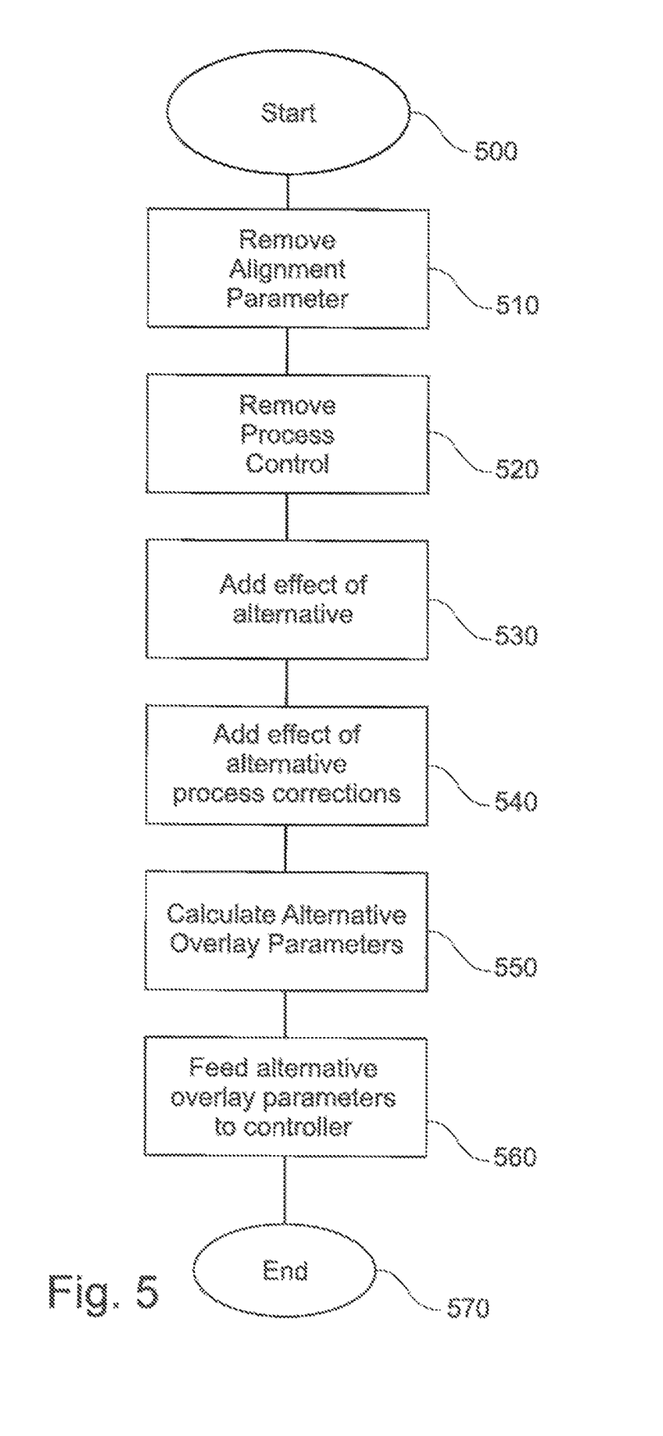
FIG. 5 shows a flow diagram of the simulation method

The simulation of the overlay is now explained in more detail with reference to FIG. 5. The simulation processor 60 has stored the alignment data, the process correction parameters and the overlay measurement results in the non-volatile memory.

The simulation starts at step 500 and in step 510 the alignment corrections, i.e. the result of the alignment, from the alignment data are subtracted from the overlay measurement results.

In step 520, the corrections due to the process control parameters are removed from the overlay measurement results subsequent to the removal of the alignment data. This results in "cleansed" overlay measurement data.

An alternative alignment model can be calculated either by a process engineer or by automatic modelling in step 530. This alternative alignment model represents an alignment model that a process engineer wishes to test or one that may be more efficient or results in improved yields. This alternative alignment model results in alternative alignment corrections that are added to the cleansed overlay measurement data calculated in step 520 to result in a modified overlay measurement. The simulation processor 60 also calculates from the alternative alignment model alternative process corrections in step 540 and these are added to the modified overlay measurement. This results in alternative overlay data. This alternative overlay data is the overlay data that would have been measured had the alternative alignment model been used in the processor of the semiconductor wafer.

The alternative overlay data can be used in step 550 in the simulation processor 60 to calculate alternative overlay parameters, such as magnification, rotation and translation that would have been used. The alternative overlay parameters can be used calculate updated process corrections for the next lot in step 560. The simulation ends at step 570.

The present disclosure further relates to a computer program product embedded on a computer readable medium. The computer program product comprises executable instructions for the measurements on the semiconductor wafers and the manufacture of wafers, as well as the simulation.

While various embodiments of the present invention have been described above, it should be understood that they have been presented by way of example, and not limitation. It will be apparent to persons skilled in the relevant arts that various changes in form and detail can be made therein without departing from the scope of the invention. For example in the present disclosure, the semiconductor wafer has been exposed to a light source, such as an ultra-violet light source. However, it is well known to use other sources of illumination, such as electron beams, x-rays or similar sources of electromagnetic energy with wavelengths much shorter than light. Thus, the present invention should not be limited by any of the above-described exemplary embodiments, but should be defined only in accordance with the following claims and their equivalents.

In addition to using hardware (e.g., within or coupled to a Central Processing Unit ("CPU"), microprocessor, microcontroller, digital signal processor, processor core, System on chip ("SOC"), or any other device) to control the exposure tool, the exposure controller and the overlay measurement tool, implementations may also be embodied in software (e.g., computer readable code, program code, and/or instructions disposed in any form, such as source, object or machine language) disposed, for example, in a computer usable (e.g., readable) medium configured to store the software. Such software can enable, for example, the function, fabrication, modelling, simulation, description and/or testing of the apparatus and methods described herein. For example, this can be accomplished through the use of general programming languages (e.g., C, C++), hardware description languages (HDL) including Verilog HDL, VHDL, and so on, or other available programs. Such software can be disposed in any known computer usable medium such as semiconductor, magnetic disk, or optical disc (e.g., CD-ROM, DVD-ROM, etc.). The software can also be disposed as a computer data signal embodied in a computer usable (e.g., readable) transmission medium (e.g., carrier wave or any other medium including digital, optical, or analogue-based medium). Embodiments of the present invention may include methods of providing the apparatus described herein by providing software describing the apparatus and subsequently transmitting the software as a computer data signal over a communication network including the Internet and intranets. It is understood that the apparatus and method described herein may be included in a semiconductor intellectual property core, such as a microprocessor core (e.g., embodied in HOL) and transformed to hardware in the production of integrated circuits. Additionally, the apparatus and methods described herein may be embodied as a combination of hardware and software. Thus, the present invention should not be limited by any of the above-described exemplary embodiments, but should be defined only in accordance with the following claims and their equivalents.

The invention claimed is:

1. A manufacturing control method for controlling an exposure tool for projecting a pattern onto a surface of a semiconductor wafer by testing lithography overlay comprising:
   storing, in a non-volatile memory connected to a simulation processor, alignment corrections resulting from aligning, with an exposure tool, the surface of a semiconductor wafer with a light source and a projection optic, prior to a lithography step;
   storing in said non-volatile memory process control parameters, provided from an exposure controller and used, in addition to alignment corrections, by the exposure tool during the lithography step for projecting a pattern onto a surface of the semiconductor wafer;
   storing in said non-volatile memory overlay measurements, the overlay measurements being determined from deviations measured between overlay marks of the semiconductor wafer, by means of an overlay measurement tool after the lithography step;
   subtracting with said simulation processor from the stored overlay measurements the alignment corrections and the process control parameters to produce cleansed overlay measurement data;
   determining an alternative alignment model;
   calculating with said simulation processor, from the alternative alignment model, alternative alignment corrections and alternative process control parameters;
   adding with said simulation processor the alternative alignment corrections and the alternative process control parameters to the cleansed overlay measurement data to produce alternative overlay data, the alternative overlay data enabling testing of lithography overlay;
   calculating with said simulation processor from the alternative overlay data updated alternative process corrections for a next lithography step; and
   using the updated alternative process corrections with the exposure tool for aligning and exposing portions of a further surface of a further one of the semiconductor wafer for projecting a pattern thereon.

2. The manufacturing control method of claim 1, further comprising visualising the alternative overlay data.

3. The manufacturing control method of claim 1, further comprising supplying the alternative process control parameters to an exposure device.

4. The manufacturing control method of claim 1, wherein the determining of an alternative alignment model comprises simulating a reduction of measurements.

5. A manufacturing control apparatus for controlling an exposure tool for projecting a pattern onto a surface of a semiconductor wafer by testing lithography overlay on a surface of a semiconductor wafer comprising:
   a non-volatile data store for storing alignment corrections, resulting from aligning, by means of an exposure tool, the surface of a semiconductor wafer with a light source and a projection optic prior to a lithography step, process control parameters, provided by an exposure controller and used, in addition to alignment corrections, by the exposure tool during the lithography step, and measured overlay data, the overlay data being determined from deviations measured between overlay marks of the semiconductor wafer by means of an overlay measurement tool; and a simulation processor for determining an alternative alignment model and calculating, from the alternative alignment model, alternative alignment corrections and alternative process control parameters, wherein the simulation processor is further configured to subtract the stored alignment corrections and the stored process control parameters from the stored measured overlay data to obtain cleansed overlay data and subsequently to add the alternative alignment corrections and the alternative process control parameters to the cleansed overlay data to obtain alternative overlay measurement data, enabling testing of lithography overlay and being usable to calculate updated alternative process corrections for a next lithography step, wherein the apparatus is connectable to the exposure tool, the exposure tool being adapted to use the updated alternative process corrections for aligning and exposing portions of a further surface of a further one of the semiconductor wafer for projecting a pattern thereon.

6. The manufacturing control apparatus of claim 5, the exposure tool further generating exposure fields on the surface of the semiconductor wafer, wherein the exposure device has an alignment measurement device for measuring alignment data of the semiconductor wafer in the exposure device and passage of the measured alignment data to the non-volatile data store.

7. The manufacturing control apparatus of claim 5, further comprising;

an overlay measurement device connection to an overlay measurement device measuring overlay data of the semiconductor wafer and passage of the measured overlay data to the non-volatile data store.

8. The manufacturing control apparatus of claim 5, further comprising:

a processor controller connection to a process controller for passage of the process control parameters to the non-volatile data store.

9. The manufacturing control apparatus of claim 6, further comprising a visualisation device for visualising the alternative overlay measurement data.

* * * * *